United States Patent [19]

Armor

[11] 4,337,358

[45] Jun. 29, 1982

[54] PROCESS FOR OXIDIZING PRIMARY AMINES TO OXIMES BY ELEMENTAL OXYGEN

[75] Inventor: John N. Armor, Morris Plains, N.J.

[73] Assignee: Allied Corporation, Morristown, N.J.

[21] Appl. No.: 254,000

[22] Filed: Apr. 13, 1981

Related U.S. Application Data

[63] Continuation-in-part of Ser. No. 164,463, Jun. 30, 1980, abandoned.

[51] Int. Cl.$^3$ .................. C07C 131/04; C07C 131/00
[52] U.S. Cl. .................................. 564/267; 564/265; 564/266; 564/268
[58] Field of Search ............... 564/253, 267, 268, 262, 564/265, 266

[56] References Cited

U.S. PATENT DOCUMENTS

| | | | |
|---|---|---|---|
| 2,706,204 | 4/1955 | Kahr | 564/268 |
| 2,886,596 | 5/1959 | Meister et al. | 564/262 |
| 3,503,958 | 3/1970 | Landis | 564/215 |

FOREIGN PATENT DOCUMENTS 47-25324  7/1972  Japan .................................. 564/268

*Primary Examiner*—Natalie Trousof
*Assistant Examiner*—L. Hendriksen
*Attorney, Agent, or Firm*—Alan M. Doernberg; Gerhard H. Fuchs

[57] ABSTRACT

Primary saturated aliphatic and alicyclic amines are oxidized by elemented oxygen to oximes, especially cyclohexylamine to cyclohexanone oxime, in vapor phase using silica gel catalyst; preferably using concentrations by volume such as 1% to 5% of amine and 5% to 30% of oxygen, and using temperatures between about 120° C. and 250° C. at atmospheric pressure.

5 Claims, No Drawings

PROCESS FOR OXIDIZING PRIMARY AMINES TO OXIMES BY ELEMENTAL OXYGEN

REFERENCE TO RELATED APPLICATION

This is a continuation-in-part of copending Ser. No. 164,463, now abandoned, filed June 30, 1980.

BACKGROUND OF THE INVENTION

This invention relates to conversion of primary saturated aliphatic and alicyclic amines having between 2 and 12 carbon atoms to oximes, comprising contacting said amine in vapor phase with elemental oxygen and a silica gel catalyst.

A Japanese patent publication of July 11th, 1972, No. SHO47-25324, relates to oxidation in liquid phase of primary aliphatic and alicyclic amines wherein a tertiary alcohol is maintained present and preferably ammonia gas is present. A catalyst such as tungstic acid, phosphotungstic acid, molybdic acid, selenic acid, or selenious acid is preferably used. Highest conversions obtained in the examples are less than 20% and yields based on oxygen consumed are less than 50%.

SUMMARY OF THE INVENTION

The present invention provides a process for conversion of primary saturated aliphatic and alicyclic amines, having between 2 and 12 carbon atoms in the molecule, to oximes, and comprises contacting said amine in vapor phase with elemental oxygen and with essentially only unreactive diluent vapors or gases at amine and oxygen concentrations outside explosive limits; and with a silica gel catalyst having surface area of between about 50 and about 1000 $m^2/g$; pressure between about 0.1 and 10 atmospheres (about 10 to about 1,000 kPa); and at temperature between about 120° C. and 250° C. The term "unreactive diluent vapors or gases" as used herein means constituents of the vapor phase which do not adversely affect conversion of the amino constituent to oxime, when the other reaction conditions are made optimum. Such vapors or gases include but are not limited to so-called inert gases such as helium, nitrogen, and rare gases; and also ammonia and water vapor.

DETAILED DESCRIPTION

When "conversion" is referred to herein, it is defined as: 100×(moles of amine consumed)/(mols of amine fed into the reactor); "selectivity" is: 100×(mols of oxime produced)/(mols of amine consumed); and "yield" is: 100×(mols of oxime produced)/(mols of amine fed into the reactor).

Preferred temperatures for our process are generally in the range between 120° C. and 250° C.; and for conversion of cyclohexylamine to cyclohexanone oxime, which is the preferred reaction in accordance with this invention, preferred temperatures are between about 135° C. and 175° C. Such temperatures allow a reasonable conversion in a contact time of the heated gaseous reactants, at reaction temperature, with the catalyst generally in the range between about 0.1 and 10 seconds, depending on the reactivity of the particular amine and the temperature employed. For cyclohexylamine, preferred contact times are from about 2 to about 6 seconds, calculated on the basis that the reaction mixture approximates a perfect gas. The pressure used is conveniently about atmospheric but can be higher or lower if desired. The concentration by volume of the reactants are usually between 0.5% and 6% amine and 5%–23% oxygen.

Amines to which our process is applicable are alicyclic amines, and especially cyclohexylamine; and also include ethylamine, n-propylamine, isopropylamine, n-butylamine, 2-aminobutane, 1-amino-3-methylbutane, 3-aminopentane, n-hexylamine, n-octylamine, laurylamine, aminocyclopentane, 1-amino-2-methylcyclohexane, 1-amino-2,6-dimethylcyclohexane, 1-amino-3,3,5,5-tetramethylcyclohexane, cyclopentylamine, cycloheptylamine, cyclooctylamine, cyclodecaamine, cyclododecaamine, diphenylmethylamine and benzylamine.

Catalysts useful in the process of the present invention include silica gels having a surface area of between about 50 and about 1000 $m^2/g$, preferably at least 100 $m^2/g$ and more preferably about 200 to about 600 $m^2/g$. The pore diameters preferably range from about 3 to about 50 mm. The best catalyst had a surface area between about 350 and about 500 $m^2/g$ and a pore diameter of about 10 mm. With these best catalysts, best results were achieved with a cyclohexylamine concentration of between about 0.5% and about 6% by volume, an oxygen concentration of between about 5% and about 23% by volume, atmospheric pressure, a temperature between about 135° C. and 175° C. and a contact time of heated gaseous reactants with catalyst between about 2 and 8 seconds. Neither temperature, pressure, contact time nor feed ratios appeared particularly critical to conversion and selectivity.

It is, however, desirable to operate with oxygen and amine volume proportions outside the explosive region. For most organics and air (i.e. about 20 volume percent oxygen), the explosive region at atmospheric pressure has a lower limit of 2–5% and an upper limit of 4–8%, varying among specific organics. Examples of this phenomena are well known in the literature, as evidenced by N. Kalkert et al., "Determination of Explosion Limits of Ammonia in Mixtures with Simple Hydrocarbons and Air, German Chem. Eng. vol. 3, pp. 53–56 (1980); W. L. Buckley et al., Chemical Eng. Prog. vol. 58, No. 2, pp. 81–84 (1962). Upper and lower limits for a particular organic amine, for a particular oxygen concentration and a particular pressure can be estimated from the literature, and determined more precisely by routine experimentation.

It is preferred to operate with an amine concentration lower than the lower limit of the explosive region. It is permissible, but less preferred to operate with more amine than the upper limit of the explosive region. The latter mode of operation has the disadvantages of requiring greater recycle and of entering the explosive region as reaction occurs, both disadvantages being less likely in the former mode of operation.

In the Example below, the reaction was carried out in a borosilicate glass tube of about 14 mm outside diameter, containing a glass frit or a plug of quartz wool to hold the catalyst in place. The glass tube reactor, equipped for downward feed of the reactants in the gas phase is cocurrent flow, was contained inside a tube furnace, electrically heated. As the catalyst is made deeper, under otherwise the same conditions, the extent of conversion increases. The depth of catalyst bed can be varied; typically it can be about 1 to 2.5 cm in depth. The temperature, measured at the wall of the furnace, was maintained practically constant at about 150° C. The reactor can be operated manually and also automatically using a cam timer to actuate the sampling valves for reactants and products.

The ketone was fed as vapor from a saturator. The products emerging from the bottom of the reactor passed through heated lines and could be diverted for analysis by gas chromatography.

EXAMPLE

The following example is illustrative of the best mode of operation as now contemplated by the inventors.

Cyclohexylamine is vaporized by passing the gases (inert gas, conveniently helium) and oxygen through a vaporizer maintained at a temperature, specifically 83° C., at which the cyclohexylamine vapor pressure provides 3% by volume of cyclohexylamine in the reaction gases. The oxygen percent was about 20% and the balance was helium gas. The flow rate of total vapors and gases at atmospheric temperature and pressure was about 21 cm$^3$/min. The reactor was set up for downward flow of the gases through a bed of catalyst, which was specifically the silica gel available as "Porasil A," 80-100 mesh, described by the manufacturer (Waters Associates of Framingham, Mass.) as having average pore diameter of 100 angstroms (10 nm) and surface area of 350-500 square meters per gram. The volume of the catalyst bed was 2 cm$^3$; and the temperature employed was about 150° C. On the basis that the heated gaseous reaction mixture approximates a perfect gas, the contact time is calculated as about 4 seconds.

The results obtained showed conversion of about 18% and selectivity of about 60%, i.e., a yield of about 11% per pass of the reaction mixture over the catalyst.

Generally similar results can be obtained with other primary saturated aliphatic and alicyclic amines, having between two and 12 carbon atoms in the molecule, by adjusting the ratios of reactants, and adjusting the temperatures and contact times within the broad ranges above indicated (120°-250° C. and 0.1-10 seconds).

Illustrative of other silica gel products, useful as the catalyst in the process of this invention, are amorphous silica gel beads having narrow ranges of pore diameters such as 4.5 nm, 7.5 nm, 12 nm and 35 nm, as in products available as "Controlled Pore Glasses" from Electro Nucleonics of Fairfield, N.J.

I claim:

1. Process for conversion of primary saturated aliphatic and alicyclic amines having between 2 and 12 carbon atoms in the molecule to oximes, comprising contacting said amine in vapor phase with elemental oxygen and with essentially only unreactive diluent vapors or gases at amine concentration and oxygen concentration outside the explosive limits; and with a silica gel catalyst having surface area of between about 50 and about 1000 m$^2$/g; at absolute pressure between about 10 and 1,000 kPa; and at temperature between about 120° C. and about 250° C.; and at contact time of the heated gaseous rectants with the catalyst between about 0.1 and 10 seconds.

2. Process of claim 1 wherein said silica gel catalyst has a surface area at least about 100 m$^2$/g.

3. Process of claim 2 wherein said silica gel catalyst has a surface area between about 200 and about 600 m$^2$/g.

4. Process of claim 1 wherein the amine is alicyclic.

5. Process of claim 4 wherein the amine is cyclohexylamine, the amine concentration is between about 0.5% and 6% by volume, the oxygen concentration is between about 5% and 23% by volume, the pressure is about atmospheric, the temperature is between about 135° C. and 175° C., the contact time of the heated gaseous reactants with the catalyst is between about 2 and 8 seconds and the catalyst has average pore diameter of about 10 nm and surface area of about 350-500 m$^2$/g.

* * * * *